US00PP33659P3

(12) United States Plant Patent
Jennings

(10) Patent No.: US PP33,659 P3
(45) Date of Patent: Nov. 23, 2021

(54) ***RUBUS* PLANT NAMED 'BONNIE LEWIS'**

(50) Latin Name: *Rubus idaeus*
Varietal Denomination: Bonnie Lewis

(71) Applicant: James Hutton Ltd., Dundee (GB)

(72) Inventor: Sophia N Jennings, Dundee (GB)

(73) Assignee: JAMES HUTTON LTD., Dundee (GB)

( * ) Notice: Subject to any disclaimer, the term of this patent is extended or adjusted under 35 U.S.C. 154(b) by 0 days.

(21) Appl. No.: 17/035,400

(22) Filed: Sep. 28, 2020

(65) Prior Publication Data

US 2021/0105922 P1 Apr. 8, 2021

(30) Foreign Application Priority Data

Oct. 8, 2019 (QZ) ..... PBR 2019/2568

(51) Int. Cl.
*A01H 5/08* (2018.01)
*A01H 6/74* (2018.01)

(52) U.S. Cl.
USPC ..... Plt./204
CPC ..... *A01H 6/7499* (2018.05)

(58) Field of Classification Search
USPC ..... Plt./204
CPC ..... A01H 6/7499
See application file for complete search history.

*Primary Examiner* — Anne Marie Grunberg
(74) *Attorney, Agent, or Firm* — Penny J. Aguirre

(57) ABSTRACT

A new cultivar of *Rubus* plant named 'Bonnie Lewis' that is characterized by its canes that have thorns that are green in color, its canes that require low chill hours to flower, its large, glossy fruits, and its early autumn primocane fruit production season.

2 Drawing Sheets

Botanical classification: *Rubus idaeus.*
Cultivar designation: 'Bonnie Lewis'.

CROSS-REFERENCE TO A RELATED APPLICATION

This application claims priority to European Community Plant Variety Office (CPVO) Plant Breeder's Rights Application No. 2019/2568 filed on Oct. 8, 2019, under 35 U.S.C. 119(f), the entire contents of which is incorporated by reference herein.

BACKGROUND OF THE INVENTION

The present invention relates to a new and distinct cultivar of *Rubus idaeus* named 'Bonnie Lewis' and will be referred to hereinafter by its cultivar name, 'Bonnie Lewis'. 'Bonnie Lewis' is a new raspberry plant grown for fruit production.

The new cultivar was derived from a controlled breeding program in Dundee, Scotland, United Kingdom. The objectives of the breeding program are to develop new raspberry cultivars suitable for the fresh fruit market, both floricane and primocane, with high fruit quality, improved agronomic qualities and increased tolerance to pathogens.

The Inventor made a cross in spring of 2012 between unnamed proprietary plants in the Inventor's breeding program; reference no. 0669B-1 as the female parent and reference no. 0994H-12 as the male parent. The Inventor selected 'Bonnie Lewis' in spring of 2015 as a single unique plant amongst the seedlings that resulted from the above cross.

Asexual propagation of the new cultivar was first accomplished by the Inventor by root cuttings in Dundee, Scotland, United Kingdom in 2015. Asexual propagation by root cuttings and tissue culture using meristematic tissue has shown that the unique features of the new cultivar are stable and reproduced true to type in successive generations.

SUMMARY OF THE INVENTION

The following traits have been repeatedly observed and represent the characteristics of the new cultivar. These attributes in combination distinguish 'Bonnie Lewis' as a new and unique cultivar of *Rubus.*

1. 'Bonnie Lewis' exhibits canes that have thorns that are green in color.
2. 'Bonnie Lewis' exhibits canes that require low chill hours to flower.
3. 'Bonnie Lewis' exhibits large, glossy fruits.
4. 'Bonnie Lewis' exhibits an early autumn primocane fruit production season.

The seed parent of 'Bonnie Lewis' differs from 'Bonnie Lewis' in having canes that are spineless, having a high chill requirement to flower, fruits that are smaller in size and fruit skin that is dull in appearance. The pollen parent of 'Bonnie Lewis' differs from 'Bonnie Lewis' in having a fruit season very late in autumn and fruits that are round in shape. 'Bonnie Lewis' can be compared to the *Rubus* cultivars 'Autumn Bliss' (U.S. Plant Pat. No. 6,597) and 'Advabertwee' (U.S. Plant Pat. Nos. 23,914 and RE46,030). Both are similar to 'Bonnie Lewis' in having an early autumn primocane fruit production season. 'Autumn Bliss' differs from 'Bonnie Lewis' in having fruit that is very darker in color, fruit that does not plug from the receptacle very easily when picking, less post, and tolerance to *Phytophthora* root rot. 'Kwanza' differs from 'Bonnie Lewis' in having fruit that begins cropping very late in autumn and fruit that does not plug from the receptacle very easily when picking.

BRIEF DESCRIPTION OF THE DRAWINGS

The accompanying colored photographs illustrate the overall appearance and distinct characteristics of the new

*Rubus*. The photographs were taken of a plant 24 months in age as grown in a polytunnel in a 10-liter container in Dundee, Scotland, United Kingdom.

Figure 1:
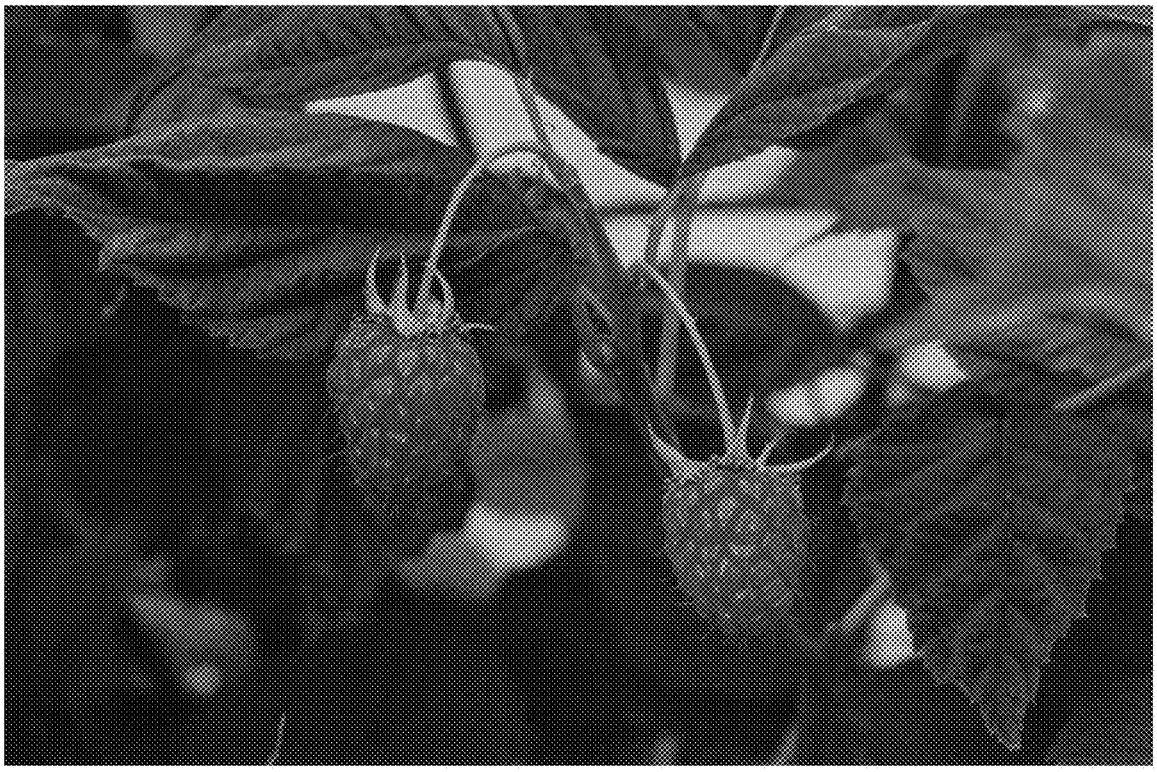

The photograph in FIG. 1 provides a view of ripe berries on a branch of 'Bonnie Lewis'.

Figure 2:
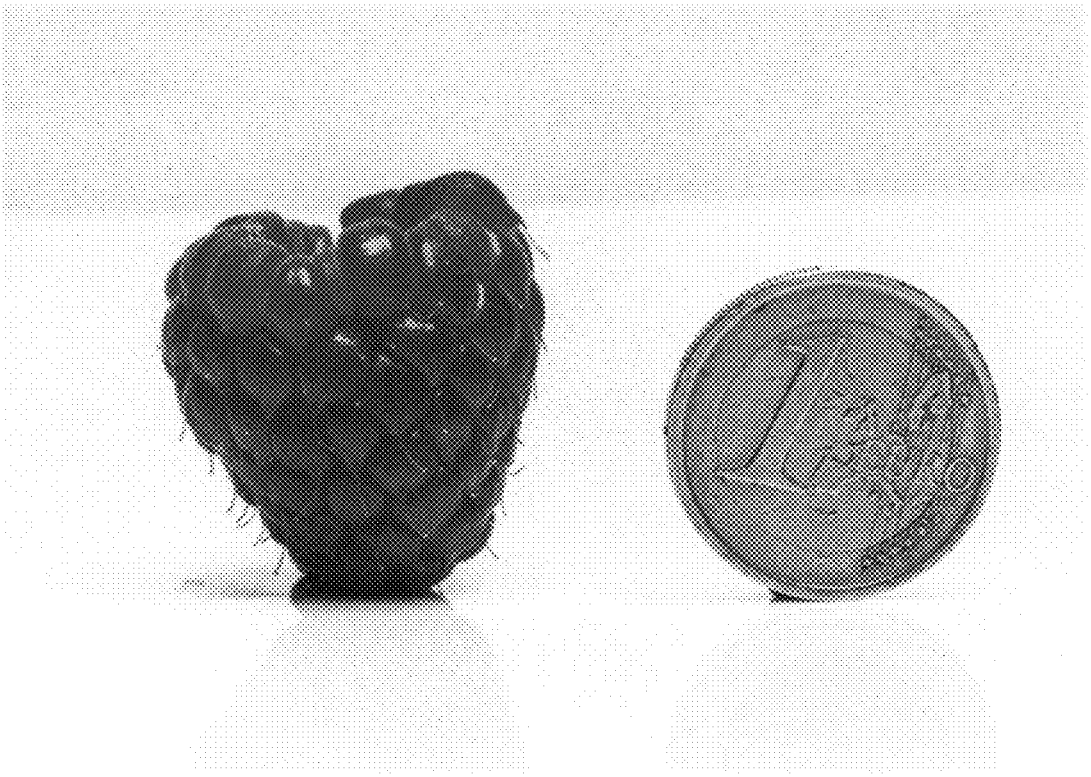

The photograph in FIG. 2 provides a close-up view of a berry of 'Bonnie Lewis'.

The colors in the photographs are as close as possible with the photographic and printing technology utilized. The colors in the photographs may differ slightly from the color values cited in the detailed botanical description, which accurately describe the colors of the new *Rubus*.

STATEMENT REGARDING PRIOR DISCLOSURES BY THE INVENTOR

The Applicant asserts that no publications or advertisements relating to sales, offers for sale, or public distribution occurred more than one year prior to the effective filing date of this application. Any information about the claimed plant would have been obtained from a direct or indirect disclosure from the Inventor. The Applicant claims a prior art exemption under 35 U.S.C. 102(b)(1) for disclosure and/or sales prior to the filing date but less than one year prior to the effective filing date. Disclosures include but may not be limited to website and facebook listings by James Hutton Ltd. and a website publication by Hortdaily.

DETAILED BOTANICAL DESCRIPTION OF THE PLANT

The following is a detailed description of plants 24 months in age as grown in a polytunnel in 10-liter containers in Dundee, Scotland, United Kingdom. The phenotype of the new cultivar may vary with variations in environmental, climatic, and cultural conditions, as it has not been tested under all possible environmental conditions. The color determination is in accordance with The 2015 Colour Chart of The Royal Horticultural Society, London, England, except where general color terms of ordinary dictionary significance are used.

General description:

*Plant type*.—Fruit producing perennial, primocane fruiting, produces fruit mainly in the autumn.

*Plant habit*.—Upright, stout canes with short internode lengths.

*Height and spread*.—An average of 2 m in height and 22 cm in spread as grown in a 10-liter container.

*Hardiness*.—This trait has not been fully characterized in a range of cold weather climates but the plants can successfully grow in western Europe (U. K. Hardiness Zone 7).

*Diseases and pests*.—Resistance to large raspberry aphid (caused by *Amphorophora idaei*) and raspberry bushy dwarf virus (RBDV) with 4 years of testing.

*Root description*.—Moderate to vigorous.

*Branching habit*.—Limited.

*Propagation*.—Root cuttings or tissue culture.

*Root development*.—An average of 2 to 3 weeks to initiate roots, an average of 5 months to fully develop as a plant with 3 canes that are 2 m in height.

*Growth rate*.—Moderate to vigorous.

Cane description

*Cane size*.—An average of 2.0 m in length and an average of 8.5 mm in width.

*Cane internode length*.—Average of 5.8 cm.

*Cane shape and aspect*.—Angled, lateral branches held at an average of 25° to 70° to vertical of main branch.

*Cane strength*.—Strong.

*Cane color*.—New canes; 144A, mature canes; 199C, internodes 199C.

*Thorns*.—1.2 mm in length with base 1.5 mm in length and 0.7 mm in width, 144A in color, distance between spines ranging between 3 mm to 10 mm in length.

*Stem surface*.—Glabrous with spines.

*Stipules*.—2 per petiole, leafy; narrowly elliptic in shape, an average of 5 mm in length and >1 mm in width, apex narrowly acute, cuneate base, upper and lower surface color 144A.

*Primocane*.—Develops in spring and initiates flower buds in late summer and develops fruit in year 1 on the top 15 to 25 buds.

Foliage description:

*Time of vegetative bud burst*.—Early season, typically about April 1st in The United Kingdom.

*Vegetative bud size*.—An average of 3.5 mm in length and 2 mm in width on current year's growth.

*Leaf shape*.—Ovate.

*Leaf arrangement*.—1 terminal and 1 to 2 lateral pairs.

*Leaf division*.—Compound, 3 to occasionally five leaflets.

*Leaf attachment*.—Petiolate.

*Leaf size*.—An average of 17 cm in length and 22 cm in width.

*Leaflet shape*.—Ovate.

*Leaflet base*.—Terminal leaflet base is cordate, lateral leaflet base ovate.

*Leaflet apex*.—Acute.

*Leaflet venation*.—Pinnate, primarily matches leaf color on upper surface and lower surface.

*Leaflet margins*.—Serrate with mucronate tip on serrations.

*Leaflet arrangement*.—1 terminal and 1 to 2 (occasionally) lateral pairs.

*Leaflet attachment*.—Primarily sessile.

*Relative position of lateral leaflet*.—Non-overlapping to slightly overlapping at base.

*Profile of leaflet cross-section*.—Slightly concave.

*Leaflet surface*.—Upper and lower surface rugose, not visibly pubescent under a handheld microscope.

*Leaflet color*.—Young; upper surface a color between 144A and 141A, lower surface 130D, mature; upper surface 141A, lower surface 130B.

*Leaflet size*.—Terminal leaf: an average of 11.2 cm in length and 13.5 cm in width.

*Petioles*.—Round in shape, an average of 4 cm in length and 2.3 cm in width, upper surface 183B, lower surface 142B, strong.

*Rachis*.—Oval in shape, an average of 4 cm in length and 4 mm in width, upper surface 183B, lower surface 142B.

Inflorescence description:

*Blooming period*.—Primocanes flower between early August and mid-September, floricanes flower from early May for 6 weeks in Scotland, United Kingdom.

*Inflorescence*.—Panicle, on upper part of plant an average of 22.4 cm in length, on lower part of plant 30.6 cm in length.

*Peduncle*.—Oval in shape, an average of 8.2 mm in length and 7 mm in width, held straight to vertical stem, color upper surface 183B, color lower surface 142B.

*Pedicels*.—Round in shape, 183B in color, an average of 1.7 cm in length and 2 mm in width, moderate to strong in strength, held in multiple angles between 90° to 180° to peduncle.

*Flower buds*.—Nearly orbicular in shape, average of 7.8 mm in length and 5.4 mm in diameter, color; immature sepals portion 144A to 144B, petal portion NN155D, surface petal portion glabrous.

*Flower type*.—Spreading calyx with center of numerous stamens and with numerous pistols, petals quickly shed upon opening.

*Flower number*.—An average of 15 to 23 flowers per lateral branch.

*Flower fragrance*.—None.

*Flower size*.—Average of 22.4 mm in height and 6 mm in diameter.

*Sepals*.—5, an average of 7 mm in length and 4 mm in width, broadly ovate to near deltoid in shape, base broad cuneate, apex aristate, entire margin, color when opening and mature 144B on upper surface and 144D on lower surface.

*Petals*.—5, an average of 5.2 mm in length, 3 mm in width, base cuneate, apex obtuse, entire margin with medium undulation, glabrous and matte on upper and lower surfaces, color; when opening and fully open upper and lower surface NN155D.

*Bracts*.—Ovate at base of pedicel, leafy; narrow elliptic in shape, an average of 18.3 cm in length and 3.3 mm in width, apex narrow acute, cuneate base, entire margin, color both surfaces 144A.

*Androecium*.—Stamens; an average of 75, filaments; 3 mm in length, NN155D in color, anthers; 1 mm in length, >1 mm in width, 11C in color, pollen; moderate in quantity.

*Gynoecium*.—Pistils; 90, average of 5 to 7 mm in length, stigmas; cup-shaped, >1 mm in length and diameter, 11C in color, style; 2 to 3 mm in length, 11C in color, ovary; 11C in color.

Fruit description:

*Fruit number*.—An average of 15 to 19 per lateral.

*Fruit shape*.—Broad conical (primocane fruit).

*Fruit texture*.—Not seedy, smooth with a good balance of juice.

*Druplets*.—An average of 79 per berry, 6 mm in length and width.

*Fruit size*.—Up to 3.8 cm in length and an average of 2.9 cm in width (primocane).

*Fruit color*.—A blend of 46A and 46B.

*Fruit adherence to plug*.—Medium.

*Fruit glossiness*.—High.

*Fruit firmness*.—Medium.

*Fruit maturity date*.—Early summer on floricanes.

*Seed*.—Reniform in shape, average of 73 per fruit, 3.6 mm in length, 2 mm in width, 159B in color.

*Cropping frequency*.—Annually, on primocanes.

*Harvest dates*.—Typically a first harvest date of August 1st and a last harvest date of September 20th when planted in a polytunnel in Dundee, Scotland, United Kingdom.

*Flavor*.—Sweet, low acid with vanilla notes.

*Fruit weight*.—6.7 g/fruit (Primocane).

*Brix*.—9.5° to 11.2°.

*Titratable acidity*.—8.5%.

*Shelf life*.—An average of 7 to 10 days after picking when kept at 4° C.

*Market use*.—Fresh fruit.

It is claimed:

1. A new and distinct cultivar of *Rubus idaeus* plant named 'Bonnie Lewis' as herein illustrated and described.

* * * * *